US005895833A

United States Patent [19]
Berg

[11] Patent Number: 5,895,833
[45] Date of Patent: *Apr. 20, 1999

[54] PRODUCTION OF HUMAN RECOMBINANT COLLAGEN IN THE MILK OF TRANSGENIC ANIMALS

[75] Inventor: Richard A. Berg, Los Altos, Calif.

[73] Assignees: Cohesion Technologies, Inc., Palo Alto, Calif.; Pharming Holding NV, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/485,194

[22] Filed: Jun. 7, 1995

Related U.S. Application Data

[60] Division of application No. 08/183,648, Jan. 18, 1994, Pat. No. 5,667,839, which is a continuation-in-part of application No. 08/011,643, Jan. 28, 1993, abandoned.

[51] Int. Cl.$^6$ .................................................. C12N 15/00
[52] U.S. Cl. ............................... 800/14; 800/7; 800/25
[58] Field of Search ....................... 800/2, 7, 14, 25; 435/69.1, 69.7, 172.3, 240.2, 240.21; 536/23.1, 24.1

[56] References Cited

U.S. PATENT DOCUMENTS

| | | | |
|---|---|---|---|
| 4,798,800 | 1/1989 | Timpl et al. | 435/273 |
| 4,873,191 | 10/1989 | Wagner et al. | 435/172.3 |
| 5,071,878 | 12/1991 | Herschler | 514/711 |
| 5,215,904 | 6/1993 | Gould et al. | 435/172.3 |
| 5,227,301 | 7/1993 | Turner et al. | 435/240.2 |
| 5,304,489 | 4/1994 | Rosen | 435/320.1 |
| 5,322,775 | 6/1994 | Clark et al. | 435/69.1 |

FOREIGN PATENT DOCUMENTS

| | | |
|---|---|---|
| 87303112 | 4/1988 | European Pat. Off. |
| PCT/GB87/00458 | 1/1988 | WIPO |
| PCT/US87/02069 | 3/1988 | WIPO |
| PCT/US88/02134 | 12/1988 | WIPO |
| PCT/EP90/01123 | 1/1991 | WIPO |
| PCT/US90/06874 | 6/1992 | WIPO |
| PCT/US92/05045 | 12/1992 | WIPO |

OTHER PUBLICATIONS

Houdebine, 1994, "Production of pharmaceutical proteins from Transgenic Animals", Journal of Biotechnology 34:269–287, 1994.

Wall, 1996, "Transgenic Livestock: Progress and Prospects for the Future", Theriogenology 45:57–68, 1996.

Thompson et al., 1989 "Germ line transmission and expression of a corrected HPRT gene produced by gene targeting in embryonic stem cells", Cell 56:313–321, 1989.

Prockop, D.J., et al., "Heritable Diseases of Collagen", The New England Journal of Medicine, 311(6):376–386 (1984).

Khillan, JS., et al, "Transgenic Mice That Express a Minigene Version of the Human Gene for Type I Procollagen (COL1A1) Develop a Phenotype Resembling a Lethal Form, of Osteogenesis Imperfacta", J. Biol. Chem. vol. 266, No. 34, pp. 23373–23379, (1991).

Olsen, AS, et al., "High Levels of Expression of a Minigene Version of the Human Proα1(I) Collagen Gene in Stably Transfected Mouse Fibroblasts", J. Biol. Chem. vol. 266, No. 2, pp. 1117–1121, (1991).

Ala–Kokko, L, et al., "Expression of a Human Cartilage Procollagen Gene (COL2A1) in Mouse 3T3 Cells", J. Biol. Chem. vol. 266, No. 22 pp. 14175–14178, (1991).

Bruggeman, LA, "Developmental Regulation for Collagen II Gene Expression in Transgenic Mice", Teratology 44:203–208 (1991).

Ebert, KM, et al., "Transgenic Production of a Variant of Human Tissue–type Plasminogen Activator in Goat Milk: Generation of Transgenic Goats and Analysis of Expression", Biotechnology 9:835–38 (1991).

Krimpenfort, P., et al, "Generation of Transgenic Dairy Cattle Using"In Vitro" Embryo Production", Biotechnology, 9:844–47 (1991.

Wright, G., et al., "High Level Expression of Active Human alpha–1–Antitrypsin in the Milk of Transgenic Sheep", Biotechnology, 9:830–34 (1991).

Robertson E.J., "Pluripotential Stem Cell Lines as a Route into the Mouse Germ Line", Trends in Genetics (TIG) (1986) 2:9–13.

Greenspan, DS., et al, "High Levels of Expression of Full Length Human Pro–α(V) Collagen cDNA in Pro–α2(V)–deficient Hamster Cells", J. Biol. Chem. 264:20683–87 (1989).

Bornstein, P., et al.. "Regulatory Elements in the First Intron Contribute to Transcriptional Control of the Human α1(I) Collagen Gene", Proc.Natl.Acad.Sci., USA, 84:8869–73 (1987).

Adams, SL., "Collagen Gene Expression", Am J. Respir.Cell & Mol.Biolo., 1:161–68 (1989).

(List continued on next page.)

*Primary Examiner*—Brian R. Stanton
*Assistant Examiner*—Deborah J. R. Clark
*Attorney, Agent, or Firm*—Richard Aron Osman

[57] ABSTRACT

Production of human procollagen or collagen in cells which ordinarily do not produce these molecules is effected by constructing expression systems compatible with mammary glands of non-human mammals. For example, expression systems can be microinjected into fertilized oocytes and reimplanted in foster mothers and carried to term in order to obtain transgenic non-human mammals capable of producing milk containing recombinant human procollagen or collagen. Human procollagen or collagen produced in this manner can be made of a single collagen type uncontaminated by other human or non-human collagens.

6 Claims, No Drawings

OTHER PUBLICATIONS

Tasanen, K., et al., "Characterization of the Human Gene for a Polypeptide That Acts Both as the β Subunit of Prolyl 4–Hydroxylase and as Protein Disulfide Isomerase", *J. Biol. Chem.* 263:16218–224 (1988).

Tasanen, K., et al., "Promoter of the Gene for the Multifunctional Protein Disulfide Isomerase Polypeptide", *J. Biol. Chem.*, 267:11513–519 (1992).

Archibald,Al., et al., High–level expression of biologically active human α1–antitrypsin in the milk of transgenic mice, *Proc.Natl.Acad.Sci., USA*, 87:5178–81 (1990).

Pittius, CW, et al. "A milk protein gene promoter directs the expression of human tissue plasminogen activator cDNA to the mammary gland in transgenic mice", *Proc.Natl.Acad. Sci., USA*, 85:5874–78 (1988).

D'Armiento, J., et al., "Collagenase expression in the lungs of transgenic mice causes pulmonary emphysema", *Cell*, 71:955–61 (1992).

Barsh, GS, et al., "DNA and chromatin structure of the human α1(I) collagen gene", *J. Biol.Chem.*, 23:14906–913 (1984).

Chu, M., et al., "Isolation of cDNA and genomic clones encoding human pro–α1(III) collagen", *J. Biol. Chem.*, 260:4357–63 (1985).

Chu, M., et al., "Human proα1(I) collagen gene structure reveals evolutionary conservation of a pattern of introns and exons", *Nature*, 310:337–340 (1984).

De Wet, W., et al., "Organization of the human pro–α2(I) collagen gene", *J. Biol.Chem.*, 262:16032–36 (1987).

Palmiter, RD, et al., "Heterologous introns can enhance expression of transgenes in mice", *Proc.Natl.Acad.Sci. USA*, 88:478–482 (1991).

Lee, S., et al., "Construction of a full–length cDNA encoding human pro–α2(I) collagen and its expression in pro–α2(I)–deficient W8 rat cells", *j. Biol.Chem.*, 263:13414–418 (1988).

Poustka A., et al., "Selective isolation of cosmid clones by homologous recombination in *Escherichia coli*", *Proc.Natl.Acad.Sci. USA*, 81:4129–33 (1984).

Bassuk, JA, et al., "Prolyl 4–hydroxylase: molecular cloning and the primary structure of the α subunit from chicken embryo", *Proc.Natl.Acad.Sci. USA*, 86:7382–86 (1989).

Helaakoski, T., et al., "Molecular cloning of the α–subunit of human prolyl 4–hydroxylase: The complete cDNA–derived amino acid sequence and evidence for alternative splicing of RNA transcripts", *Proc.Natl.Acad.Sci. USA*, 86:4392–96 (1989).

Miller, EJ., et al., "Preparation and characterization of the different types of collagen" *In:Methods in Enzymology*, 82:33–64 (1982).

Sage, H., et al., "Preparation and characterization of procollagens and procollagen–collagen intermediates" *In: Methods in Enzymology*, 82:96–127 (1982).

Stacey et al., perinatal Lethal Osterogenesis Imperfacta in Transgenic Mice Bearing an Engineered Mutant pro–α1(1) Collagen Gene:, *Nature*, 332:131–36 (1988).

Hennighausen, L., "The mammary gland as a bioreactor: production of foreign proteins in milk", *Protein Expression and Purification*, 1:3–8 (1990).

Fisler, J.S., et al., "Plasma Concentration of Amino Acids in Obese Men", (Abstract), *Int. Obes.*, 9(5):335–46, (1985).

Clark, A.J., et al., "Pharmaceuticals from Transgenic Livestock", *TIBTECH* 5:20–24, (1987).

Schmidhauser, C., et al., "Extracellular matrix and hormones transcriptionally regulate bovine β–casein 5' sequences in stably transfected mouse mammary cells", *Proc.Natl.Acad..Sci. USA* 87:9118–22 (1990).

Sigma Chemical Catalog, p. 274, (1992), Sigma Chemical Co..

PRODUCTION OF HUMAN RECOMBINANT COLLAGEN IN THE MILK OF TRANSGENIC ANIMALS

This is a divisional application of a application, Ser. No. 08/183,648, filed on Jan. 18, 1994, U.S. Pat. No. 5,667,839, which is a continuation-in-part of U.S. Ser. No. 08/011,643 filed Jan. 28 1993, now abandoned, the contents of which are incorporated herein by reference.

TECHNICAL FIELD

The invention relates to production of recombinant proteins, specifically collagen, in the milk of a transgenic mammal. More specifically, it concerns methods to prepare purified forms of useful human collagen by effecting the secretion of the collagen (or procollagen) into the milk of a transgenic mammal.

BACKGROUND ART

Collagen is a major structural protein useful in reconstructive therapeutic procedures in humans. Collagens used for these purposes are generally prepared by isolating the material from tissues of farm animals such as cows or pigs. While such isolated collagen has been used with some success, it is essentially a protein foreign to the treated human being and immunogenic responses can be a problem. This problem has been minimized by treating the animal-derived collagen with proteolytic enzymes to decrease immunogenicity.

It is clear that it would be advantageous to supply human rather than bovine or porcine collagen for therapeutic purposes. The sources for purified human collagen are limited and the only reliable source is human placenta. Human collagen can be purified from human placenta as described in copending U.S. Pat. No. 5,428,022 (Collagen Corporation). The placenta contains several types of collagens, most notably types I, III, IV, and V. The process of separating and purifying one type from the others is imperfect and results in a predominant type with small amounts of the other types. Production of purified collagen from placentas further necessitates additional processing steps to ensure that the resulting collagen product is free from human viruses such as hepatitis and HIV. In view of this, there have been attempts to prepare human collagen using recombinant techniques.

Expression of the human cartilage procollagen gene (Col2A1) in mouse 3T3 cells been reported (Ala-Kokko, L. et al., *J Biol Chem* (1991) 266:14175–14178). Olsen, A. S. et al. reported expression of a minigene version of the human proα1(I) collagen gene in mouse fibroblasts (Olsen, A. S. et al., *J Biol Chem* (1991) 266:1117–1121). Full-length human proα2(V) collagen cDNA in proα2(V)-deficient hamster cells was reported by Greenspan, D. S. et al., *J Biol Chem* (1989) 264:20683–20687; mouse fibroblasts have also been used to express the proα1(I) chain wherein the resulting expressed protein is complexed in the collagen triple helix with murine proα2(I) chains, as described by Schnieke et al., *Proc Natl Acad Sci* USA (1987) 84:8869–8873. Transgenic mice that were modified to contain a mutated form of the proα1(I) gene were not viable after birth, according to a study by Stacey, A. et al. *Nature* (1988) 322:131–136. In addition, transgenic mice have been obtained that express a minigene version of the human gene for type I procollagen systemically (Khillan, J. S. et al., *J Biol Chem* (1991) 266:23373–23379); PCT application WO92/22333. These mice are useful as model systems for investigating bone diseases characterized by the modified collagen produced.

The production of recombinant human collagen is made troublesome by the necessity for a multiplicity of posttranslational enzymes which are generally believed to be present only in cells which natively produce collagen. At least eight such posttranslational enzymes are believed to be needed (Prockop et al., *New England J Med* (1984) 311:376–386). This has limited attempts at recombinant production to cells which natively produce this protein; this inevitably results in chimeric forms of the protein.

In order to avoid chimeric collagens which contain partly human and partly host mammalian cell chains in the triple helix, it might be possible to use human cells for this production. Even in this case, however, it is not possible to obtain collagen product of a particular type free of other collagen types. As further described below, the variety of collagens produced and their innate similarity makes homogeneous preparations from either native or recombinant sources which produce their own collagen impossible.

The present invention solves these problems by effecting the synthesis of human procollagen or collagen in cells which do not natively produce this protein, employing techniques established for the production of foreign proteins in mammalian milk, as described in the publications cited hereinbelow. The collagen of designated types is secreted into the milk either as procollagen or collagen, depending on the construction of the expression systems and accompanying recombinant enzyme production.

DISCLOSURE OF THE INVENTION

The invention provides recombinant production of human collagen in a form that permits isolation of a homogeneous collagen type and can be designed to effect the production of commercially practical amounts of these proteins at a reasonable cost. The invention utilizes systems developed for the production of recombinant proteins in mammalian milk and requires utilization of these techniques not only to effect the expression of the gene encoding the desired collagen, but also, if required, expression of the gene for any required posttranslational enzymes.

Thus, in one aspect, the invention is directed to a method for the recombinant production of human procollagen or collagen comprising recovering milk from the mammary glands of a nonhuman mammal. The mammal will have been modified to contain an expression system that comprises DNA encoding human procollagen under the control of regulatory sequences operable in mammary glands. The human procollagen or collagen produced is recovered from the milk by various purification techniques. The nonhuman mammal may also be modified if necessary to contain an expression system for the production of any needed posttranslational enzymes in the milk protein-secreting cells of the mammary glands.

Either collagen or procollagen may be secreted depending on the presence or absence of suitable proteases in the cell. The procollagen encoded in the nucleotide sequence contained in the expression system will be preceded by a nucleotide sequence encoding an appropriate signal, either that natively associated with the procollagen or an alternate signal sequence workable in the targeted cells. Thus, the procollagen produced as a result of a recombinant expression will be secreted into the milk. If the host cells contain enzymes which ordinarily effect cleavage of the prosequences from collagen—i.e. procollagen N-protease and/or procollagen C-protease, the procollagen will be cleaved of the prosequences as it exits the cell and collagen will be secreted into the medium. However, if these enzymes are absent from the production cell, procollagen itself will be secreted. Low levels of these proteases will result in mixtures of collagen and procollagen. Apparently the levels of these enzymes vary in cells which natively produce collagen. Depending on the tissue and the developmental stage of the subject from which the tissue originates, a greater or lesser proportion of procollagen or collagen will be contained in the secreted materials. Thus, the milk which contains the collagen of the invention will contain this collagen in the form of human collagen per se, human procollagen per se or a mixture of both.

While it would be possible to modify the native procollagen genes to delete the coding sequences for the prosequences, it is not desirable to do this since the pro-region, especially the C-terminal pro-region, mediates the formation of triple helixes by the collagen portion of the molecule. Thus, if the prosequences are deleted from the expression vector, the resulting single collagen chains would be unable to form the triple helix which characterizes the collagen molecules.

If procollagen is secreted into the milk, of course, by supplying the appropriate proteolytic enzymes, collagen will result.

In another aspect, the invention is directed to expression systems useful in the foregoing method which comprise a DNA sequence encoding human procollagen operably linked to a promoter and other regulatory sequences capable of effecting expression in mammary glands. If necessary, expression systems operable in mammary glands for production of posttranslational enzymes can also be used. The invention also is directed to nonhuman embryonic stem (ES) cells and to nonhuman eggs, including fertilized forms, modified to contain the expression system as well as to the nonhuman mammal implanted with the fertilized egg or with a blastula including the ES cells.

In other aspects, the invention is directed to milk containing human procollagen or collagen, and to homogeneous forms of human procollagen or collagen. These forms are made available by the practice of the invention method which permits the production of only the recombinant collagen type desired absent a background of either similar nonhuman collagen molecules, or of collagens of different types.

MODES OF CARRYING OUT THE INVENTION

Collagen is a well studied protein, and the expression of genes encoding collagen has also been reviewed recently (Adams, S. L., *Amer J Respir Cell and Molec Biol* (1989) 1:161–168). This review summarizes the types of collagen known to occur and describes their common features. The mRNAs encoding collagens of various types are translated in the cytoplasm of collagen-producing cells into procollagen subunits which are then assembled into triple helices. The assembled procollagen contains propeptide extensions at the N and C termini that help to assemble the subunits, but do not participate in the triple helix. The prosequences are then cleaved to obtain collagen triple helix as the procollagen is secreted. The collagen helix itself contains nonhelical extensions designated telopeptides. The triple helical regions contain repeating amino acid sequences with a glycine in every third position and proline (P) or hydroxyproline (HP) often in the other positions so as to contain a sequence of "triplets" of the form —(GXY)$_n$—, wherein X or Y or both are P or HP. One of the essential posttranslational steps is the conversion of some proline residues to hydroxyproline to ensure stability of the triple helix at body temperature. Other important posttranslational modifications are disulfide exchange, hydroxylation of lysyl residues, addition of carbohydrate and the assembly and crosslinking of the triple helical collagen molecules.

According to the Adams review, thirteen genetically distinct collagen types have been described and represent the products of at least 23 genes. The most common types found in interstitial tissues are types I, III, V and VI; in cartilage, types II, IX, X and XI are found. Some of these types exist natively as homotriplexes; others are heterotriplexes.

The nomenclature for the various collagen types is designed to designate the genetic origin of the collagen in question. For example, the triple helix of type I collagen is a heterotriplex containing the products of two different collagen-encoding genes. This type of collagen is designated $[\alpha_1(I)]_2 \alpha_2(I)$; thus, type I collagen triplexes contain two chains encoded by the Col1A1 gene and one protein chain encoded by the Col1A2 gene. Type III collagen is designated $[\alpha_1(III)]_3$ and is thus comprised of three identical chains translated from the Col3A1 gene. Type II collagen is also a homopolymer designated $[\alpha_1(II)]_3$ which is comprised of translation products of the Col2A1 gene.

Since collagen-producing cells, as described above, produce several types of collagen, it has, in the past, been impossible to obtain, for example, homogeneous type I collagen free of type III collagen. By producing collagen in noncollagen-producing cells according to the method of the invention, obtaining such homogeneous preparations becomes possible.

The genetic materials for use in the method of the invention encoding the desired collagens are available. The genes encoding human types I, II, III, IV and V collagen are currently available.

Prockop, D J et al. (supra) list the following cotranslational and posttranslational modifications that occur when collagen is produced in fibroblasts: cleavage of signal peptides at the N-termini of the chains, hydroxylation of the Y-position proline and lysine residues, hydroxylation of a few X-position proline residues, addition of galactose or galactose and then glucose to some of the hydroxylysines, addition of a mannose-rich oligosaccharide to the C propeptides, association of the C-terminal propeptides through a process directed by a structure of these domains, and finally formation of both intrachain and interchain disulfide bonds in the propeptides. After secretion of the procollagen, the N propeptides are cleaved by a procollagen N proteinase and the C propeptides by a separate procollagen C proteinase. The collagen then self-assembles into fibrils, and lysyl oxidase converts some lysine and hydroxylysine residues to the aldehyde derivatives to form crosslinks with similar residues in adjacent molecules.

It is not entirely clear whether mammary cells, since they do not endogenously produce collagen, contain the enzymes necessary for these posttranslational events. Since the assembly into triplexes is mediated by the sequences of the C-terminal extensions, in the event the epithelial cells of the mammary glands lack the required proteases, it is believed that the assembly into triplexes can be effected extracellularly by providing appropriate secretion signals to the procollagen molecule as stated above and adding suitable proteases. Alternatively, the proteases could be produced recombinantly in the epithelial mammary cells. The enzymes most likely to be needed by the mammary cells in order to effect required posttranslational processing are protein disulfide isomerase and the α-subunit of prolyl hydroxylase. If these enzymes are not endogenously produced and must be provided recombinantly, expression systems for their production may be supplied along with the expression systems for the collagen or procollagen itself. The gene for the α-subunit of prolyl hydroxylase has not yet been completely described but the gene encoding the protein disulfide isomerase has been partially sequenced as described by Tasanen, K., et al, *J Biol Chem* (1988) 263:16218–16224 and *J Biol Chem* (1992) 267: 11513–11519. Genes encoding both proteins can be obtained using standard techniques. These two enzymes function together as a tetrameric protein comprising two subunits of prolyl hydroxylase noncovalently associated with two α subunits of protein disulfide isomerase. Although the two subunits of protein disulfide isomerase are functional as a dimer, the two α subunits of prolyl hydroxylase must be associated with protein disulfide isomerase in order to be active (Vuari, et al., 1992).

A well developed system for use in the invention method utilizes milk production in cows. This system is summarized by Krimpenfort, P. et al. in *Biotechnology* (1991) 9:844–847. This article describes microinjection of fertilized bovine oocytes with genes encoding human proteins and development of the resulting embryos in surrogate mothers. The human genes were fused to the bovine $\alpha S_1$ casein regulatory elements. This general technology was also described in PCT Application WO91/08216 published Jun. 13, 1991 and assigned to GenPharm.

Additional descriptions of the production of recombinant proteins by developing transgenic animals which secrete the proteins into milk are found in European Application 264166 published Apr. 20, 1988, assigned to Integrated Genetics. This disclosure emphasizes use of whey acid protein control systems to effect protein secretion and cites use of this system for the production of tPA and Hepatitis B surface antigen in goat milk. Analogous systems for production of foreign proteins are described in PCT application WO88/00239 published Jan. 14, 1988 and assigned to Pharmaceutical Proteins Limited. This application describes procedures for obtaining suitable regulatory DNA sequences for the products of the mammary glands of sheep, including beta lactoglobulin, and describes the construction of transgenic sheep modified so as to secrete foreign proteins in milk. An additional application, PCT WO88/01648, published Mar. 10, 1988 and assigned to Immunex Corporation, generally describes construction of transgenic animals which secrete foreign proteins into milk under control of the regulatory sequences of bovine alpha lactalbumin gene. Finally, PCT application WO88/10118, published Dec. 29, 1988 and assigned to Biogen, describes construction of transgenic mice and larger mammals for the production of various recombinant human proteins in milk. Other publications which describe the production of various proteins in milk include Archibold, A. L. et al. *Proc Natl Acad Sci* USA (1990) 87:5178–5182 which describes production of human α-antitrypsin in the milk of transgenic mice. This production utilized a hybrid gene constructed from the β-lactoglobulin gene fused to an α1-antitrypsin minigene. Pittius, C. W. et al. *Proc Natl Acad Sci* USA (1988) 85:5874–5878 describe production of tissue plasminogen activator in the mammary glands of transgenic mice using the murine whey acidic protein promoter. Hennighausen, L. *Protein Expression and Purification* (1990) 1:3–8 provides a review of the use of the mammary gland as a bioreactor and the production of various foreign proteins in milk. This article describes the factors that affect the level of production and indicates recommended forms of expression system construction. The disclosures of the foregoing publications are incorporated herein by reference.

Thus, techniques for construction of appropriate host vectors containing regulatory sequences effective to produce foreign proteins in mammary glands and cause the secretion of said protein into milk are known in the art. In addition, techniques for constructing transgenic mammals containing these systems, including mice as well as larger mammalian species such as cows, sheep and goats, are well known.

Systems for the expression of the procollagen gene in cells that produce milk protein can be constructed using methodology analogous to that recently described for the production of human collagenase in the lungs of transgenic mice (D'Armiento et al., *Cell* (1992) 71:955–961).

Genes encoding a number of procollagen types have been obtained; and genes for additional types can be obtained similarly. The preparation and cloning of the human Col1A1 gene has been described (Barsh et al., *J Biol Chem* (1984) 259:14906–14913). Briefly, a human genome cosmid library is packaged and used to transduce *E. coli*, which are plated, grown, and screened using a nucleic acid sequence specific for the Col1A1 gene. Positive colonies are located, matured in broth, and the DNA isolated. Restriction endonucleases are used to cut the DNA at selected sites. The digested DNA is examined by gel electrophoresis and DNA sequencing. A cosmid clone CG 103 isolated from a human genomic library was shown to contain the entire human Col1A1 gene.

Fragments of collagen genes have been selected from cosmid libraries (Barsh et al., supra) and from bacteriophage libraries (Chu et al., *J Biol Chem* (1985) 260:4357–4363 for type III collagen; Chu et al., *Nature* (1984) 310:337–340 for type I collagen). The Col1A1 gene was obtained in three overlapping genomic clones using the Charon 4A bacteriophage vector. The Col1A2 gene has also been obtained from five overlapping clones in Charon 4A libraries (deWet et al., *J Biol Chem* (1987) 262:16032–16036). It has been shown that the first intron is important in regulating the α1(1) gene expression in a tissue-specific manner in transgenic mice (Slack, J. L. et al. *Mol Cell Biol* (1991) 11:2066–2074).

As an alternative to using the entire gene, full-length cDNAs could be used, although the use of the entire gene has been shown to be more effective in transgenic animal experiments (Palmiter et al., *Proc Natl Acad Sci* USA (1991) 88:478–482). Such a full-length cDNA can be isolated from cDNA libraries, as was done for the cDNA for the alpha-2 chain of type I collagen (Lee et al., *J Biol Chem* (1988) 263:13414–13418), which was isolated from a lambda phage library.

To construct an expression system compatible with the epithelial cells of mammary glands, the Col1A1 or other procollagen gene, as a DNA fragment is ligated to a similarly prepared DNA fragment containing the promoter and any additional required regulatory sequences for a milk-specific protein expression. As described by D'Armiento et al., when ligating a promoter to a gene, it is necessary to preserve the translational start site for the protein. This may be accomplished by introducing a specific restriction endonuclease site immediately preceding the translation start site that is also unique for the 5' end of the chosen promoter. When these fragments are prepared using such a restriction endonuclease, the sites at the 3' end of the promoter will be compatible with the 5' end of the Col1A1 gene. When ligation occurs, the promoter will be ligated at the correct site of the gene to encode a messenger RNA that will allow translation from the translation start site of the procollagen gene, analogous to ligation of the heptoglobin promoter to the human collagenase gene described by D'Armiento et al., supra. The promoter-gene construct is ligated into a bacteriophage vector cloning system by treating the phage DNA with a restriction endonuclease; both ends of the foreign DNA are then ligated to the vector construct for cloning the DNA.

CDNA containing the translation start site for expressed messenger RNA can also be ligated to a promoter to prepare a functional construct for introduction into a transgenic animal. This method was used for the human lactoferrin cDNA fused to the bovine alpha S1-casein gene 5' and 3' untranslated regions (Krimpenfort).

It is also understood that upstream regions of the promoter may be involved in regulating gene expression. Specifically, it has been shown that the extracellular matrix and hormones regulate the expression of bovine β-casein by their influence on the upstream sequences in the relevant gene (Schmidhauser, C. et al. *Proc Natl Acad Sci* USA (1990) 87:9118–9122). In addition, signals for termination of transcription and translation are also helpful in elevating levels of expression.

In order to reduce the size of the procollagen gene so that the construct could be cloned in bacteriophage, the gene itself could be shortened by reducing the size of the introns. This could be done for procollagen genes that are cloned as overlapping fragments. The introns at the junction sites of the fragments could be identified and treated with specific endonuclease to shorten the introns, but leave restriction sites that are compatible for ligation. Restriction sites could be altered by site-directed mutagenesis (D'Armiento et al., supra) to generate restriction sites for ligation of the fragments of the procollagen gene into a single construct. Another method of accomplishing the removal of introns is to prepare fusion genes containing cDNAs to replace two or more exons within the gene.

One of the posttranslational modifying enzymes necessary for the production of collagen is protein disulfide isomerase, which, when combined with the alpha subunit of prolyl hydroxylase, forms a tetrameric protein isolated as prolyl hydroxylase. The gene for protein disulfide isomerase has been obtained from a human genomic library produced in a cosmid vector pcos 2EMBL (Poustka et al., *Proc Natl Acad Sci* USA (1984) 81:4129–4133). The library was screened with cDNA fragments specific for human protein disulfide isomerase and several clones were obtained, at least two of which contained the entire gene (Tasanen et al., *J Biol Chem* (1988) 263:16218–16224).

For use in the expression systems of the invention, this gene can be cut from the cosmid DNA with restriction endonucleases and ligated to a milk-specific protein promoter using a strategy similar to that used for the construct of the heptoglobin-collagenase DNA.

In the event that the mammary cells are unable to provide suitable enzymes for posttranslational modification of the procollagen produced, the transgenic animals would need to be modified with expression systems for these enzymes. Construction of these expression systems is analogous to that described herein for procollagen gene expression. The expression systems for the posttranslational enzymes are provided to the transgenic animal along with the expression systems for the desired collagen product.

The choice of a promoter for expression in milk would preferably be from one of the milk-specific proteins, such as alpha S1-casein 5' and 3' regulatory sequences, which were fused to the human lactoferrin cDNA, providing a construct that used the alpha S1-casein promoter and signal sequence for the human lactoferrin gene. Another construct used to express a foreign protein in sheep milk consisted of the sheep beta-lactoglobin promoter fused to human and antitrypsin gene fragments (Wright et al., *Biotechnology* (1991) 9:830–833). A third promoter that has been used is the whey acid promoter, which was fused to cDNA for a modified version of human tissue plasminogen activator (Ebert et al., *Biotechnology* (1991) 9:835–838) and used to prepare transgenic goats in whose milk human tissue plasminogen activator was expressed. The sequence of the gene is scanned for available unique restriction endonuclease sites, which are selected so that the functional gene containing the precise translation start site is preserved in the mRNA.

In the event that it is desirable to provide posttranslational enzymes in the mammary cells, it is believed that the most important candidates are prolyl hydroxylase and protein disulfide isomerase. The gene for the chick alpha subunit of prolyl hydroxylase has not yet been completely isolated, but is known to be as large as 50 kb (R. A. Berg unpublished information). It is expected that the entire gene may be obtained from a human genomic cosmid library, as was done for the Col1A1 gene and the gene for protein disulfide isomerase. The cDNA for chick alpha subunit (Bassuk et al., *Proc Natl Acad Sci* USA (1989) 86:7382–7386) and human alpha subunit (Helaakoski, T., *Proc Natl Acad Sci* USA (1989) 86:4392–4396) have been described. Since the gene is not yet available, the cDNA for the human alpha subunit for prolyl hydroxylase can be fused to the promoter for a milk-specific protein to produce a DNA construct for introduction into a transgenic animal.

Using these systems, animals are obtained which secrete human collagen or procollagen into milk. The gene encoding the desired procollagen chain is coupled to suitable control sequences which function in the mammary cells of mammalian species such as the regulatory sequences associated with the αS1 casein gene, β-lactalbumin or α-lactalbumin genes, β-lactoglobin or lactoferrin genes. Both 5' and 3' regulatory sequences can be used. The genes encoding the required posttranslational enzymes are similarly constructed into expression systems using mammary cell-specific regulatory sequences.

The resulting expression systems are microinjected using, for example, the technique described in U.S. Pat. No. 4,873,191. The expression system constructs are amplified by PCR or cloning and purified by agarose gel electrophoresis. After electroelution, the concentration is adjusted to 1–10 µg/ml and microinjected into the oocytes which are obtained from ovaries freshly removed from cows or other animals. The oocytes are aspirated from the follicles and allowed to settle before fertilization with thawed frozen sperm capacitated with heparin and prefractionated by Percoll gradient to isolate the motile fraction.

The fertilized oocytes are centrifuged, for example, for eight minutes at 15,000×g to visualize the pronuclei for injection and then cultured from the zygote to morula or blastocyst stage in oviduct tissue-conditioned medium. This medium is prepared by using luminal tissues scraped from oviducts and diluted in culture medium. The zygotes must be placed in the culture medium within two hours following microinjection.

Estrous is then synchronized in the intended recipient mammals such as cattle by administering coprostanol. Estrous is produced within two days and the embryos are transferred to the recipients 5–7 days after estrous.

Successful transfer can be evaluated in the offspring by Southern blot. By utilizing this system to effect the expression of the Col1A1 gene, for example, the offspring can be evaluated for the presence of the Col1A1 gene by Southern hybridization using a Col1A1 gene derived probe.

Alternatively, the desired constructs can be introduced into embryonic stem cells (ES cells) and the cells cultured to ensure modification by the transgene. The modified cells are then injected into the blastula embryonic stage and the blastulas replaced into pseudopregnant hosts. The resulting offspring are chimeric with respect to the ES and host cells, and nonchimeric strains which exclusively comprise the ES progeny can be obtained using conventional cross-breeding. This technique is described, for example, in PCT Application WO91/10741, published Jul. 25, 1991.

For production of the desired procollagen or collagen in milk, expression systems for both the procollagen gene and the posttranslational enzyme-encoding genes must be present in the transgenic animal. There are several ways to achieve this.

First, the mammalian host may already produce the required levels of posttranslational enzymes in the epithelial cells of the mammary glands. Alternatively, the constructs to be microinjected into eggs or transfected into ES cells may include a cocktail of the desired procollagen gene expression system along with the expression systems similarly constructed for, for example, the prolyl hydroxylase and protein disulfide isomerase. The successful production of collagen in the milk can then be determined using antiprocollagen antibodies or by analysis of the milk for levels of hydroxyproline, a unique amino acid found in collagen as a result of the activity of prolyl hydroxylase.

In another alternative, the expression systems for the procollagen gene and the expression systems for any needed posttranslational enzyme-encoding genes may be injected into different batches of fertilized eggs or transfected into different batches of ES cells and used separately as described above to develop transgenic animals capable of expressing the procollagen or collagen genes and the posttranslational enzyme-encoding genes, respectively. These transgenic animals can then be crossbred and the offspring evaluated for the ability to express both such systems. At least some of the offspring of such transgenic animals will be capable of producing both the collagen product and the posttranslational enzyme product.

In still another approach, fertilized eggs or ES cells may be prepared from transgenic animals already modified to have the capacity to express one or the other of the procollagen genes or the posttranslational enzyme-encoding genes. These eggs can then be microinjected or the ES cells transfected with the expression system for the proteins lacking in the transgenic animal to develop into a transgenic animal containing expression systems for all of the required components.

Similarly, transgenic animals already modified with respect to one desired gene may be used as sources for the blastulas into which modified ES cells are implanted. Again, chimeric animals will result which can be used in crossbreeding to obtain offspring having genes for all of the desired proteins.

It may be noted that the expression systems for both of the particular posttranslational enzymes described above, if needed, must be provided essentially simultaneously since the enzymes function together as a tetrameric protein; as described above, the two α subunits of prolyl hydroxylase must be associated with protein disulfide isomerase in order to be active.

When suitable transgenic mammals have been obtained by any of the foregoing methods, the procollagen or collagen is secreted into the milk. The procollagen or collagen product of the transgenic mammal will be determined by the nature of the procollagen gene in the expression system provided. For homotriplexes, only a single gene is inserted. For production of heterotriplexes, such as typical human collagen type I, either both the Col1A1 and Col1A2 genes are utilized in the original microinjection, or mammals transgenic for human Col1A1 are crossbred with mammals transgenic for human Col1A2. The type III collagen gene Col3A1 can be used to prepare a transgenic animal and may be simpler because only one collagen polypeptide chain is required.

For the procollagen genes provided in the expression systems, procollagen is secreted into the milk if the required proteases for conversion to collagen are absent. To the extent that these protease enzymes are absent from the secreting epithelial cells and are not provided for by recombinant systems, procollagen is secreted into the milk and can be recovered in a manner analogous to procedures that would be used for collagen per se. The procollagen can also be converted before or after purification using specific proteases to cleave the prosequences as is known in the art. On the other hand, if the proteases are natively present intracellularly or are provided by recombinant systems, collagen will be secreted directly. Depending on the levels of these enzymes, mixtures of procollagen and collagen may be obtained in the milk which can, if desired, be converted by treatment of the milk with proteases to convert all of the relevant molecules to collagen per se.

As described above, previous preparations of human collagen of a given type are always contaminated by the presence of alternative type collagens in view of the similarity of these materials and in view of the capacity of native or other recombinant cells previously used to produce collagens encoded by their own genomes. By use of the method of the invention, it is possible to obtain collagen or procollagen of a given type free from coexpressed collagens or procollagens of alternative types.

Purification of collagen or procollagen from milk is accomplished using their characteristic solubility and chemical properties. For example, milk may be acidified, causing milk-specific proteins such as casein to precipitate and collagen or procollagen to remain in solution. The collagen or procollagen may be precipitated from acid solutions by the addition of salt, alcohol, or propylene glycol. (Miller, E. J. and Rhodes, R. K., *Methods in Enzymology* (1982) 82:33–64); Sage, H. and Bernstein, P., ibid., 96–127.)

I claim:

1. A method of preparing a single type of trimeric human procollagen, collagen, or a mixture of such procollagen and collagen, which method comprises the step of:

recovering said procollagen, collagen, or mixture from milk of a transgenic mammal comprising an expression system comprising a coding nucleotide sequence encoding a human procollagen polypeptide chain operably linked to a control nucleotide sequence that effects expression specifically in milk protein-secreting epithelial cells of a mammary gland in said mammal, and said cells express said coding nucleotide sequence to produce said polypeptide chain, and secrete said procollagen, collagen, or mixture comprising said chain in said milk without extracellular aggregation of said procollagen, collagen or mixture which would prevent excretion from said mammary gland.

2. The method of claim 1, wherein said control nucleotide sequence comprises a bovine alpha S1-casein promoter DNA sequence.

3. The method of claim 2, wherein said single type of human procollagen is human Type I procollagen and said single type of human collagen is human Type I collagen.

4. A transgenic nonhuman mammal whose somatic and germ cells contain an expression system comprising a coding nucleotide sequence encoding a human procollagen polypeptide chain operably linked to a control nucleotide sequence that effects expression specifically in milk protein-secreting epithelial cells of a mammary gland in said mammal, and said cells express said coding nucleotide sequence to produce said polypeptide chain, and secrete a single type of human procollagen, collagen, or a mixture thereof into the milk of said mammal, wherein said milk comprises trimeric collagen, procollagen, or a mixture thereof, in recoverable amounts without extracellular aggregation which would prevent excretion from said mammary gland.

5. The transgenic nonhuman mammal of claim 4, wherein said single type of human procollagen is human Type I procollagen and said single type of human collagen is human Type I collagen.

6. The transgenic nonhuman mammal of claim 4, wherein said promoter is a bovine alpha S1-casein promoter.

* * * * *